(12) United States Patent
Nilsson et al.

(10) Patent No.: US 7,557,234 B2
(45) Date of Patent: Jul. 7, 2009

(54) PROCESS FOR THE PREPARATION OF ALKYL PHOSPHINATES

(75) Inventors: Maths Nilsson, Södertälje (SE); Mats Thelin, Södertälje (SE); Johanna Wachtmeister, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 119 days.

(21) Appl. No.: 11/575,082

(22) PCT Filed: Sep. 12, 2005

(86) PCT No.: PCT/SE2005/001316

§ 371 (c)(1),
(2), (4) Date: May 4, 2007

(87) PCT Pub. No.: WO2006/031180

PCT Pub. Date: Mar. 23, 2006

(65) Prior Publication Data

US 2008/0319231 A1 Dec. 25, 2008

(30) Foreign Application Priority Data

Sep. 13, 2004 (SE) .................................. 0402199

(51) Int. Cl.
*C07F 9/02* (2006.01)
(52) U.S. Cl. ....................................................... 558/89
(58) Field of Classification Search .................... 558/89
See application file for complete search history.

(56) References Cited

U.S. PATENT DOCUMENTS 4,933,478 A * 6/1990 Wardleworth et al. ....... 558/104
2004/0167330 A1    8/2004 Lukes et al.

FOREIGN PATENT DOCUMENTS

EP        307362 B1      2/1995

OTHER PUBLICATIONS

Deprèle et al., "A Novel and Convenient Preparation of Hypophosphite Esters", Journal of Organometallic Chemistry, vol. 643-644, p. 154-163, 2002.
Fitch, Steven J., "Synthesis of Hypophosphite Esters from Orthocarbonyl Compounds", Journal of the American Chemical Society, vol. 86, p. 61-64, 1964.
Gallagher et al., "Organophosphorus Intermediates. VI. The Acid-Catalysed Reaction of Trialkyl Orthoformates with Phosphinic Acid", Aust. J. Chem, vol. 33, p. 287-294, 1980.

* cited by examiner

*Primary Examiner*—Jafar Parsa
(74) *Attorney, Agent, or Firm*—White & Case LLP

(57) ABSTRACT

The invention relates to a new process for the production of alkyl dialkoxyalkylphosphinates. A hypophosphite salt is used in the process.

8 Claims, No Drawings

PROCESS FOR THE PREPARATION OF ALKYL PHOSPHINATES

FIELD OF THE INVENTION

The present invention is directed to a new process for the production of alkyl dialkoxyalkylphosphinates.

BACKGROUND OF THE INVENTION

The production of ethyl (diethoxymethyl) phosphinate has been described in Gallagher, M. J. Honegger, H. *Aust. J. Chem.* 1980, 33, 287-294 (see below). The phosphinic acid was obtained by evaporation of commercial aqueous solutions (50 wt % water).

EP 307362 A2 describes the production of aliphatylphosphinic acid derivatives from aqueous phosphinic acid.

A process for esterification of hypophosphite salts has been published in Deprèle, S. Montchamp, J.-L. *J. Organomet. Chem.* 2002, 643-644. 154-165 and is outlined below:

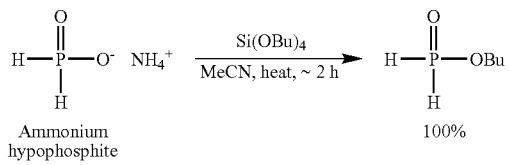

Ammonium hypophosphite     100%

One object of the present invention was to develop a process for the production of alkyl dialkoxyalkylphosphinates that is more suitable for large-scale production.

Outline of the Invention

The present invention is directed to a new process for the production of alkyl dialkoxyalkylphosphinates of formula (I):

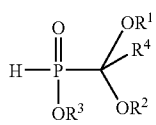

(I)

wherein
$R^1$, $R^2$ and $R^3$ each and independently represents methyl or ethyl; and
$R^4$ represents hydrogen or methyl;
whereby a hypophosphite salt is reacted with a compound of formula (II):

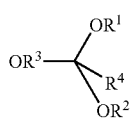

(II)

wherein
$R^1$, $R^2$, $R^3$ and $R^4$ are as defined above;
in the presence of a solvent and an acid.

The process according to the present invention may be used for the synthesis of inter alia ethyl (diethoxymethyl) phosphinate. By using this method the hazardous handling of neat phosphinic acid can be avoided. Further, the amount of by-products may be controlled.

Methods of Preparation

In one embodiment of the invention, the compound of formula (II) is charged to a stirred slurry of hypophosphite salt and a suitable solvent such as toluene-ethanol (20:1). The mixture is carefully inerted and acid is charged at a controlled speed. The slurry is stirred at from 0° C. to 20° C. during 1 to 20 hours or until most of the intermediate alkyl ester is consumed. The mixture is quenched by the addition of aqueous sodium hydrogen carbonate and the organic layer is concentrated.

In one embodiment of the present invention, the hypophosphite salt is selected from ammonium hypophosphite, sodium hypophosphite and potassium hypophosphite.

In one embodiment of the present invention, the compound of formula (II) is selected from trimethylorthoformate, triethylorthoformate, trimethylorthoacetate and triethylorthoacetate.

In one embodiment of the present invention, the acid used in the reaction is selected from methane sulphonic acid, sulphuric acid, boron trifluoride etherate and trifluoromethane sulphonic acid. In a further embodiment of the invention, the acid is essentially water-free. In one embodiment, the acid contains up to 10% water, up to 5% water or up to 2% water.

In one embodiment, the solvent used in the process according to the present invention is toluene, acetonitrile, tetrahydrofuran (THF), methylene chloride, benzene or a mixture of toluene and ethanol.

EXAMPLES

Synthesis of ethyl(diethoxymethyl)phosphinate using methane sulphonic acid

Triethylorthoformate (42.1 mL, 253 mmol, 2.1 eq) was added to a cold (0° C.) mixture of finely ground ammonium hypophosphite (10 g, 120 mmol, 1.0 eq), toluene (50 mL) and ethanol (3.5 mL) under a nitrogen atmosphere. The slurry was inerted and cooled to about 0° C. Methane sulphonic acid (8.4 mL, 127 mmol, 1.05 eq) was charged (exothermic) during 4 minutes ($T_i$ was kept below 10° C.). The slurry was stirred at 0° C. and after 1 hour GC-analysis showed 93% conversion from the ethylester to the desired product. After 2 hours, the reaction mixture was quenched with saturated aqueous sodium hydrogen carbonate (37 mL). After phase separation the organic layer was concentrated under reduced pressure at 40° C. to a colourless liquid containing ~50% toluene (28.0 g, GC-purity 95%, assay 51.2%). (Amount of ethyl (diethoxymethyl) phosphinate: 14.3 g, 73.1 mmol, yield ~61%).

$^{13}$C-NMR (CD$_3$CN): δ 14.2 (2×CH$_3$), 15.4 (CH$_3$), 62.4+62.5 (CH$_2$O), 64.5+64.6 (CH$_2$O), 64.9+65.0 (CH$_2$O) and 99.1+100.5 (CHO$_2$). $^{31}$P-NMR: δ 26.8 (ddd).

Synthesis of ethyl(diethoxymethyl)phosphinate using methane sulphonic acid in 2-L-scale Triethylorthoformate (632 mL, 3.80 mol, 2.1 eq) was added to a cold (0° C.) mixture of ammonium hypophosphite (150 g, 1.81 mol, 1.0 eq), toluene (750 mL) and ethanol (75 mL) under a nitrogen atmosphere. The slurry was inerted and cooled to ~0° C. Methane sulphonic acid (126 mL, 1.90 mol, 1.05 eq) was charged (exothermic) during 8 minutes ($T_i$ was kept below 10° C.). The slurry was stirred at 0° C. and after 1 hour GC-analysis showed 90% conversion from the ethylester to the desired product. After 1.5 hours, the reaction mixture was quenched with saturated aqueous sodium hydrogen carbonate (600 mL). After phase separation the organic layer was concentrated under reduced pressure at 40° C. to a colourless liquid containing ~65% toluene (579 g, GC-purity 88%, assay 34.4%). (Amount of ethyl (diethoxymethyl) phosphinate: 199.2 g, 1.02 mol, yield ~56%).

Synthesis of ethyl(diethoxymethyl)phosphinate using methane sulphonic acid in 500-L-Scale Triethylorthoformate (133.6 kg, 901.4 mol, 2.1 eq) was charged to a cold (0° C.), vigorously stirred mixture of ammonium hypophosphite (35.6 kg, 429.2 mol, 1.0 eq), toluene (107 L) and ethanol (11 L) under a nitrogen atmosphere. The slurry was carefully inerted while cooled to ~0° C. The slurry was then continuously purged with nitrogen in order to reduce the amount of oxidized by-products. Methane sulphonic acid (43.3 kg, 450.7 mol, 1.05 eq) was then charged (exothermic) during 30 minutes ($T_i$ was kept below 10° C.). The slurry was stirred at 0° C. and after 2.5 hours the reaction mixture was quenched by a controlled charge ($T_i \leqq 10°$ C.) of a mixture with sodium hydrogen carbonate (14.4 kg, 171.7 mol, 0.4 eq) and water (128 L). The charging vessel was rinsed with water (14 L) and the reaction mixture was stirred vigorously during 10 minutes After phase separation the organic layer was concentrated under reduced pressure at 40° C. to ~⅓ of the volume. (82 L, 0.991 kg/L, 81.3 kg, GC-purity 89.6%, assay 61%). (Amount of ethyl (diethoxymethyl) phosphinate: 49.6 kg, 252.7 mol, yield 58.9%).

Synthesis of ethyl(diethoxymethyl)phosphinate using sulphuric acid

Concentrated sulphuric acid (1.65 mL, 29.7 mmol, 0.5 eq) was charged to a mixture of ammonium hypophosphite (5 g, 60.2 mmol, 1 eq), toluene (45 mL) and ethanol (5 mL) at ambient temperature. After 2 hours triethylorthoformate (26.0 mL, 156.3 mmol, 2.6 eq) was added and the slurry was stirred over night. GC-analysis showed almost complete conversion of the intermediate ethylester to the desired product. The reaction mixture was then quenched with a 1:1 mixture of saturated aqueous sodium hydrogen carbonate and brine (50 mL). The phases were separated and the organic layer was washed twice, first with the 1:1 mixture of saturated aqueous sodium hydrogen carbonate and brine (50 mL) and then with only brine (25 mL). The organic layer was then dried ($Na_2SO_4$) and concentrated under reduced pressure. Ethyl (diethoxymethyl) phosphinate was isolated as a colourless oil. (5.7 g, GC-purity ~93%, yield ~44%).

Synthesis of ethyl(diethoxymethyl)phosphinate using boron trifluoride-etherat Boron trifluoride etherate (3.47 mL, 13.3 mmol, 1.1 eq) was charged during 3 minutes to a mixture of ammonium hypophosphite (1 g, 12.0 mmol, 1 eq), toluene (8 mL), ethanol (2 mL) and triethylorthoformate (5.2 mL, 25.2 mmol, 2.1 eq). The reaction was stirred at ambient temperature and after 4 hours GC-analysis showed good conversion to the desired product.

Synthesis of ethyl(diethoxymethyl)phosphinate using trifluoro methanesulphonic acid Trifluoromethane sulphonic acid (1.2 mL, 13.6 mmol, 1.1 eq) was charged during 3 minutes to a cold (0° C.) mixture of ammonium hypophosphite (1 g, 12.0 mmol, 1 eq), toluene (10 mL) and triethylorthoformate (4.2 mL, 31.3 mmol, 2.6 eq). The reaction was stirred at ambient temperature and after 2 hours GC-analysis showed good conversion to the desired product. The product was not isolated.

Synthesis of ethyl(diethoxyethyl)phosphinate using methane-sulphonic acid

Triethylorthoacetate (4.6 mL, 25.1 mmol, 2.1 eq) was added to a cold (0° C.) mixture of ammonium hypophosphite (1.0 g, 12.0 mmol, 1.0 eq) and toluene (5 mL). The slurry was cooled to ~0° C. and inerted. Methane sulphonic acid (0.84 mL, 12.7 mmol, 1.05 eq) was charged (exothermic) during 4 minutes ($T_i$ was kept below 10° C.). The reaction was stirred at 0° C. and after 1 hour GC-analysis showed ~40% conversion to the desired product. After 3 hours the reaction mixture was quenched by the addition of saturated aqueous sodium hydrogen carbonate (3.6 mL). After phase separation the organic layer was concentrated to a colourless oil (1.1 g, GC-purity ~81%, yield ~35%).

$^{13}$C-NMR ($CD_3CN$): δ 14.4 (2×$CH_3$), 15.4 ($CH_3$), 18.0 ($CH_3$), 57.0+57.1 ($CH_2O$), 57.4+57.5 ($CH_2O$), 62.5+62.6 ($CH_2O$) and 98.9+100.4 ($CHO_2$). $^{31}$P-NMR: δ 30.0 (dm).

Synthesis of methyl(dimethoxyethyl)phosphinate using methane-sulphonic acid

Trimethylorthoacetate (3.2 mL, 25.1 mmol, 2.1 eq) was added to a cold (0° C.) mixture of ammonium hypophosphite (1.0 g, 12.0 mmol, 1.0 eq) and toluene (5 mL). The slurry was cooled to ~0° C. and inerted. Methane sulphonic acid (0.84 mL, 12.7 mmol, 1.05 eq) was charged (exothermic) during 4 minutes ($T_i$ was kept below 10° C.). The reaction was stirred at 0° C. and after 1 hour GC-analysis showed ~50% conversion to the desired product. After 3 hours the reaction mixture was quenched by the addition of saturated aqueous sodium hydrogen carbonate (3.6 mL). After phase separation the organic layer was concentrated to a colourless oil (0.21 g, GC-purity ~92%, yield ~10%).

$^{13}$C-NMR ($CD_3CN$): δ 17.0+17.1 ($CH_3$), 48.8+48.9 ($CH_3O$), 49.2+49.3 ($CH_3O$), 52.5+52.6 ($CH_3O$) and 99.2+100.7 ($CHO_2$). $^{31}$P-NMR: δ 32.4 (dm).

Synthesis of methyl(dimethoxymethyl)phosphinate using methane-sulphonic acid Trimethylorthoformate (2.8 mL, 25.6 mmol, 2.1 eq) was added to a cold (0° C.) mixture of ammonium hypophosphite (1.0 g, 12.0 mmol, 1.0 eq) and toluene (5 mL). The slurry was cooled to ~0° C. and inerted. Methane sulphonic acid (0.84 mL, 12.7 mmol, 1.05 eq) was charged (exothermic) during 4 minutes ($T_i$ was kept below 10° C.). The reaction was stirred at 0° C. and after 1 hour GC-analysis showed ~84% conversion to the desired product. After 3 hours the reaction mixture was quenched by the addition of saturated aqueous sodium hydrogen carbonate (3.6 mL). After phase separation the organic layer was concentrated to a colourless oil (0.12 g, GC-purity ~78%, yield ~7%).

$^{13}$C-NMR ($CD_3CN$): δ 48.4 ($CH_3O$), 56.3 ($CH_3O$), 56.4 ($CH_3O$) and 101.4+102.9 ($CHO_2$). $^{31}$P-NMR: δ 31.6 (dm).

The invention claimed is:
1. A process for the production of an alkyl dialkoxyalylphosphinate of formula (I):

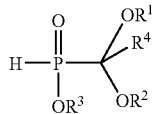

(I)

wherein:

$R^1$, $R^2$ and $R^3$ are each independently selected from methyl and ethyl; and $R^4$ is selected from hydrogen and methyl;

wherein the process comprises reacting a hypophosphite salt with a compound of formula (II):

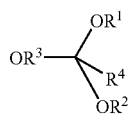

(II)

wherein $R^1$, $R^2$, $R^3$ and $R^4$ are as defined above, in the presence of toluene, or a mixture of toluene and ethanol, and an acid containing less than 5% water, and wherein the process is performed at a temperature of from 0° C. to 20° C.

2. The process according to claim 1, wherein the hypophosphite salt is selected from the group consisting of ammonium hypophosphite, sodium hypophosphite, and potassium hypophosphite.

3. The process according to claim 1, wherein the compound of formula (II) is selected from the group consisting of trimethylorthoformate, triethylorthoformate, trimethylorthoacetate, and triethylorthoacetate.

4. The process according to claim 1, wherein the acid is selected from the group consisting of methane sulphonic acid, sulphuric acid, boron trifluoride etherate, and trifluoromethane sulphonic acid.

5. The process according to claim 1, wherein the acid contains less than 2% water.

6. The process according to claim 1, wherein the process is performed over a period of from 1 to 20 hours.

7. The process according to claim 1, wherein $R^1$ is ethyl; $R^2$ is ethyl; and $R^3$ is ethyl.

8. The process according to claim 1, wherein $R^4$ is hydrogen.

* * * * *